Jan. 6, 1948. A. BURKWOOD Plant Pat. 776
VIBURNUM HYBRID PLANT
Filed Nov. 29, 1946
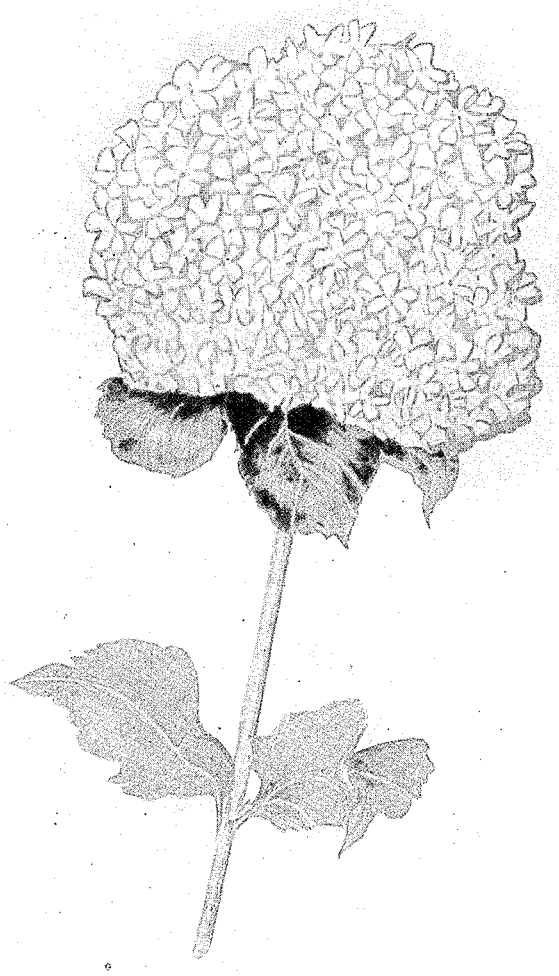
INVENTOR
ALBERT BURKWOOD
BY Oberlin & Limbach
ATTORNEYS.

Patented Jan. 6, 1948

Plant Pat. 776

UNITED STATES PATENT OFFICE

776

VIBURNUM HYBRID PLANT

Albert Burkwood, Rotherfield, England, assignor to John J. Grullemans

Application November 29, 1946, Serial No. 712,821

1 Claim. (Cl. 47—60)

This invention relates to a new variety of viburnum hybrid plant.

The present viburnum hybrid plant was produced by me by crossing a viburnum carlesii as the seed parent with a viburnum macrocephalum as the pollen parent, the former being a species of viburnum from China and the latter being a species of viburnum from Japan.

The plant was first developed by me at Kingston on Thames, England, the viburnum carlesii being crossed with the pollen taken from the viburnum macrocephalum (true form). The resulting large flat flower heads bore both fertile and sterile flowers and a number of the seeds therefrom were planted and, from the seedlings thereof, the present variety was selected and asexually reproduced by grafting on roots.

The plant was first asexually reproduced by me at Rotherfield, Sussex, England.

*The drawing*

The single figure is an elevation of a portion of one of the stalks of the plant showing the flower head and leaves thereon.

*The plant generally*

The plant has fibrous roots of average size and depth, their lateral spread being about equal to the lateral spread of the exposed portion of the plant, as is usual for this type of plant.

The plant has good resistance to disease, wetness, and drouth, and its winter resistance, unprotected, is exceptional, specimens having withstood temperatures of 16° F. below freezing.

The exposed portion of the plant is a compact bushy shrub of regular contour having approximately an average height of six feet and a maximum spread of six feet. Its growth is vigorous and it has good resistance unprotected to low temperatures as well as to disease, drouth and wetness. It prefers moderate sun but will grow well in the shade or in northern or southern exposures. It prefers a loamy soil having normal drainage, but in general, it is rather indifferent to types of soil.

The main stalks of the plant are upright and woody and very much branched. They are relatively stiff and tough for this type of plant and adequate to support well the foliage and bloom. The new growth is pale green, darkening with age, the old growth being a dark green or brown. The color is generally uniform for a given stalk. The main stalks vary in length from 2½ to 6 feet on the average, having a smooth surface texture and growth singly from the roots. They are oppositely branched, the branches being generally grayish with a smooth surface texture. The leaves are arranged oppositely and are of average quantity. The new leaves are generally pale green on top, comparable to Maerz and Paul Plates 22–H–8 through 22–J–6, the older leaves being darker green. On the under side the leaves generally are gray. The color is uniform for each leaf. The leaves are of average size, varying in length from two to three inches and in width from one and one half to two inches. They are of average thickness and smooth on both the upper and lower faces. They persist well on the plant. Generally, they are quite similar to the leaves of viburnum carlesii. The pedicels or leaf stems are smooth and average about one fourth inch in length and are very strong.

The plant blooms well throughout a wide range geographically. For best blooming it prefers sun but it will bloom well under any exposure in which the plant itself grows well. The best blooms are produced, however, in a well drained rich moist loamy soil but there is no great difference in quality due to average changes in these conditions. The number, size and color of the blooms does not appear to be affected materially by sun, shade, moisture, heat and cold conditions. The blooming period generally is throughout May and June during which the plant blooms continuously.

The buds are of average size and globular and supported in upright position on the stems. When the sepals first divide, the buds are pink but this color changes to white when the petals begin to unfurl and, when the plant is in bloom, the flowers are white. The sepals are usual for the type of plant and the calyx is rather large and globular with the usual smooth texture. The peduncles average from one and one half to two inches in length and are relatively strong. They have smooth surfaces and are pale green in color. The same is true of the pedicels. The flowers are relatively slow in opening and this habit is not appreciably affected by temperature or weather. The blooms average from three and one half to four inches in diameter and as many as forty are produced on a plant four feet in height.

The florets are borne in single globular heads and their permanence on the plant and as cut flowers is very similar to that of the parents. Each floret has four petals which, at their outer portions, are pink in the bud shading to pure white as the floret opens. The base of the petals is white throughout the blooming period and there is little difference in coloring on opposite sides. They are of the usual form and arrangement and of smooth texture. The blooms have a pronounced and very sweet aroma or fragrance which lasts well both in cut and uncut flowers.

The fruit of the plant is of the usual form and color, but sparse.

The plant is characterized particularly in its extreme hardiness, the exceptional strength of the main stalk or trunk, its free blooming characteristics, its exceptionally large heads of white flowers, its fragrance, its ruggedness which makes it very easy to grow in practically any exposure and under any of the usual garden conditions.

I claim:

The new and distinct variety of viburnum hybrid plant herein shown and described and characterized particularly in its extreme hardiness, the exceptional, strength of the main stalk or trunk, its free blooming characteristics, its exceptionally large heads of white flowers, its sweet and lasting fragrance and its ruggedness which makes it very easy to grow in practically any exposure under any of the usual garden conditions.

ALBERT BURKWOOD.